(12) United States Patent
Olson

(10) Patent No.: US 6,940,076 B2
(45) Date of Patent: Sep. 6, 2005

(54) SYSTEM FOR, AND METHOD OF, IRRADIATING ARTICLES

(75) Inventor: Dennis G. Olson, Omaha, NE (US)

(73) Assignee: The Titan Corporation, San Diego, CA (US)

(*) Notice: Subject to any disclaimer, the term of this patent is extended or adjusted under 35 U.S.C. 154(b) by 240 days.

(21) Appl. No.: 09/872,441

(22) Filed: Jun. 1, 2001

(65) Prior Publication Data

US 2002/0179853 A1 Dec. 5, 2002

(51) Int. Cl.[7] .................. G01N 23/00; G01N 21/00
(52) U.S. Cl. ................ 250/455.11; 250/453.11; 250/454.11; 378/69
(58) Field of Search ............. 250/453.11, 454.11, 250/455.11; 378/69

(56) References Cited

U.S. PATENT DOCUMENTS

| 4,983,849 | A | | 1/1991 | Thompson et al. |
| 5,396,074 | A | | 3/1995 | Peck et al. |
| 5,400,382 | A | * | 3/1995 | Welt et al. ............. 378/69 |
| 6,215,847 | B1 | * | 4/2001 | Perrins et al. ............ 378/69 |

FOREIGN PATENT DOCUMENTS

| WO | WO 99/67793 | 12/1999 |
| WO | WO 00/68955 | 11/2000 |
| WO | WO 01/00249 A1 | 1/2001 |
| WO | WO 01/25754 A1 | 4/2001 |

OTHER PUBLICATIONS

US 5 396 074 a (Peck Richard O et al.)—Relevant to Claim No. 1–52 Mar. 7, 1995, cited in the application column 1, line 13 –column 1, line 18 column 4, line 52 –column 6, line 37; figures 1, 2.

* cited by examiner

*Primary Examiner*—John R. Lee
*Assistant Examiner*—Paul M. Gurzo
(74) *Attorney, Agent, or Firm*—Peter K. Hahn; David E. Heisey; Luce, Forward, Hamilton & Scripps

(57) ABSTRACT

An article has irregular characteristics such as an irregular geometrical configuration. Radiation from a radiation source is directed in a particular direction toward the article. The radiation energy passing from the source to the article at different positions in the article is absorbed in accordance with the irregularities in the characteristics of the article at the different positions to maintain the radiant energy at the different positions in the article within particular limits. For irregularities of a geometrical configuration in the article, the absorption may be provided by a fixture having a geometrical configuration which constitutes the difference at every position between a substantially constant value and the geometrical configuration of the article at this position. The absorption may be provided by conveying the article and the fixture past the radiation source in a direction substantially perpendicular to the particular direction.

41 Claims, 2 Drawing Sheets

SYSTEM FOR, AND METHOD OF, IRRADIATING ARTICLES

This invention relates to systems for, and methods of, irradiating products, including food products, to make them safe to use or eat. The invention particularly relate to systems for, and methods of, providing the irradiation within particular limits regardless of irregularities in the characteristics, including irregularities in the geometric shape, of the products including the food products.

BACKGROUND OF A PREFERRED EMBODIMENT OF THE INVENTION

It has been known for some time that drugs and medical instruments and implements have to be irradiated so that they will not cause patients to become ill from harmful bacteria when they are applied to the patients. Systems have accordingly been provided for irradiating drugs and medical instruments and implements. The drugs and the medical instruments and implements have then been stored in sterilized packages until they have been ready to be used.

In recent years, it has been discovered that foods can carry harmful bacteria if they are not processed properly or, even if they are processed properly, that the foods can harbor and foster the proliferation of such harmful bacteria if they are not stored properly or retained under proper environmental conditions such as temperature. Some of the harmful bacteria can even be deadly.

For example, harmful bacteria have been discovered in recent years in hamburgers prepared by one of the large hamburger chains. Such harmful bacteria have caused a number of purchasers of hamburgers at stores in the chain to become sick. As a result of this incident and several other similar incidents, it is now recommended that hamburgers should be cooked to a well done state rather than a medium rare or rare state. Similarly, harmful bacteria have been found to exist in many chickens that are sold to the public. As a result of a number of incidents which have recently occurred, it is now recommended that all chickens should be cooked until no blood is visible in the cooked chickens.

To prevent incidents such as discussed in the previous paragraphs from occurring, various industries have now started to irradiate foods before the goods are sold to the public. This is true, for example, of hamburgers and chickens. It is also true of fruits, particularly fruits which are imported into the United States from foreign countries.

In previous years, gamma rays have generally been the preferred medium for irradiating various articles. The gamma rays have been obtained from a suitable material such as cobalt and have been directed to the articles to be irradiated. The use of gamma rays has had certain disadvantages. One disadvantage is that irradiation by gamma rays is slow. Another disadvantage is that irradiation by gamma rays is not precise. This results in part from the fact that the strength of the source (e.g. cobalt) of the gamma rays decreases over a period of time and that the gamma rays cannot be directed in a sharp beam to the article to be irradiated. This prevents all of the gamma rays from being useful in irradiating the articles.

In recent years, electron beams have been directed to articles to irradiate the articles. Electron beams have certain advantages over the use of gamma rays to irradiate articles. One advantage is that irradiation by electron beams is fast. For example, a chub having a square cross section can be instantaneously irradiated by a passage of an electron beam of a particular intensity through the chub. Another advantage is that irradiation by an electron beam is relatively precise because the strength of the electron beam remains substantially constant even when the electron beam continues to be generated over a long period of time.

X-rays have also been used to irradiate articles. The x-rays may be formed from electron beams. An advantage in irradiating articles with x-rays is that the articles can be relatively thick. For example, x-rays can irradiate articles which are thicker than the articles which are irradiated by electrons.

A problem has occurred in the past whether the irradiation has been provided by gamma rays, electrons or x-rays. This has occurred when the articles have had irregular characteristics such as irregular geometrical configurations. For example, a chub is generally circular in vertical section. This has caused the thickness of the chub to be different at every position in a radial direction in the cylindrical shape of the chub. These differences in thickness have affected the radiation which the chubs have received at the different positions.

The radiation received at every position in an article should be within particular minimum and maximum limits. If the radiation received at any position within the article is below the particular minimum limit, the harmful bacteria in the article are not destroyed. If the radiation received at any position in the article is above the particular maximum limit, quality or organoleptic characteristics of the article may be adversely affected. It is difficult to maintain the radiation dose in the article within the particular minimum and maximum limits when the article has irregularities in the characteristics at the different positions such as irregularities in the geometric configuration of the article. For example, a chub having a cylindrical configuration may be considered to have irregularities in characteristics because the vertical dimensions of the chub at the progressive positions of the chub in the horizontal direction are different.

BRIEF DESCRIPTION OF A PREFERRED EMBODIMENT OF THE INVENTION

An article has irregular characteristics such as an irregular geometrical configuration. Radiation from a source is directed in a particular direction toward the article. The radiation energy passing from the source to the article at different positions in the article is absorbed in accordance with the irregularities in the characteristics of the article at the different positions to maintain the dosage absorbed at the different positions in the article within particular limits.

For irregularities of a geometrical configuration in the article, the absorption may be provided by a fixture having a geometrical configuration which constitutes the difference at every position between a substantially constant value and the geometrical configuration of the article at this position. The absorption may be provided by conveying the article and the fixture past the radiation source in a direction substantially perpendicular to the direction of the radiation from the source.

DETAILED DESCRIPTION OF A PREFERRED EMBODIMENT OF THE INVENTION

Figure 1:
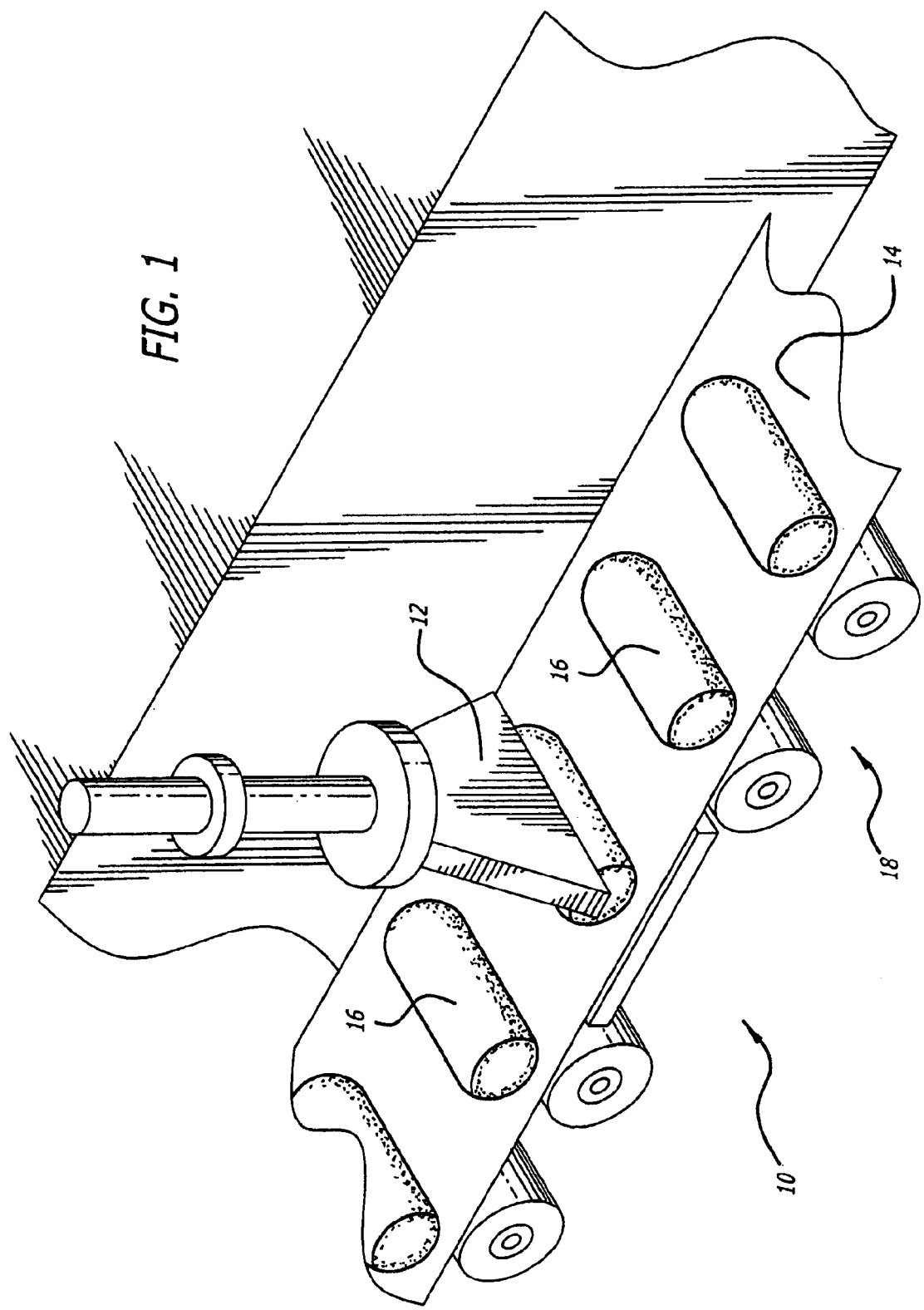
FIG. 1 is a simplified perspective view showing a system of the prior art for conveying an article (e.g. a chub) past a source of radiation to irradiate the article.

FIG. 1 is a simplified diagram of an irradiation system, generally indicated at 10, of the prior art for conveying an article past a source of radiation 12. For example, the conveyor system may be constructed as shown and described in U.S. Pat. No. 5,396,074 issued on Mar. 7, 1995, and assigned of record to the assignee of record of this application. The conveyor system 10 includes a conveyor 14 for moving articles 16 (e.g. chubs) past the radiation source 12 for irradiation of the articles by the source. The articles may be moved past the radiation source at a substantially constant speed within particular limits. The distance between successive articles on the conveyor 14 may be maintained at a minimal value within particular limits. The articles 16 may be irradiated with gamma rays, electrons or x-rays or any other type of radiation without departing from the scope of the invention.

The articles 16 may have irregular characteristics at different positions. These irregular characteristics may include irregularities in geometrical configuration. For example, the articles 16 may constitute chubs having a cylindrical shape. The radiation from the source may pass through each chub in a vertical direction corresponding to the circular cross sections of the chub.

Figure 2:
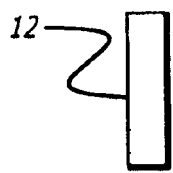
FIG. 2 is a simplified view illustrating how a system of the prior art irradiates an article such as a chub having a circular configuration in a vertical section.
Figure 2:
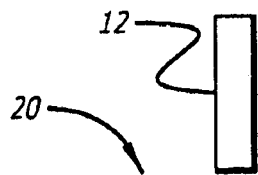

FIG. 2 illustrates a cross section view of the article 16 in the vertical direction when the article is a chub. The chub moves in a direction 17 past the accelerator 12. The direction is perpendicular to the direction of the radiation from the accelerator 12. As will be seen, the irradiation provided at a position A in a vertical section of the chub 16 is different from the irradiation provided at a position B in a vertical section of the chub even though the positions A and B are at the same distance in FIG. 2 from the accelerator 12 when the positions A and B are aligned with the accelerator. This results from the fact that the radiation has to pass through the chub 16 between the positions C and A on the one hand when the chubs move at positions C and A past the accelerator. On the other hand, the radiation has to pass only through the distances between D and B as the chub moves at the positions D and B past the accelerator.

The irradiation of the chub at the position A is accordingly different than the irradiation of the chub at the position B. This may cause the chub to be under-radiated at some positions in the chub and to be over-radiated at other positions in the chub. Under radiating in the chub is undesirable because harmful bacteria in the chub are not killed. Over-irradiating is undesirable because the quality or organoleptic characteristics of the chub may be negatively affected. It is accordingly desirable to radiate the article within particular minimum and maximum limits. This causes harmful bacteria to be killed and the quality or organoleptic characteristics of the chub to be retained.

Opposite sides of the chub 16 may be irradiated by having the chub irradiated from an opposite side of the chub. However, irradiating the chub from opposite sides of the chub does not have any effect on the dissimilarities of the radiation at the positions A and B. The reason is that the distance between E and A is the same as the distance between C and A and the distance between F and B is the same as the distance between D and B. As will be appreciated, the positions between C, A and E define a straight line and the positions between D, B and F also define a straight line. The direction between the positions C and E, and between the positions D and F, is substantially parallel to the direction of the radiation from the accelerator 12.

Co-pending application Ser. No. 09/710,730 filed in the U.S. Patent Office on Nov. 10, 2000 and assigned of record to the assignee of record of this application discloses and claims a member disposed between a radiation source and an article. The member absorbs the radiation from the accelerator, when the radiation is above the preferred maximum limit, so that the radiation passing through the source to the article will be within the preferred maximum and minimum limits in the article. However, the member is stationary.

This invention provides a simple but ingenious solution to the problems discussed above. In accordance with one embodiment shown in FIG. 3, the article 16 (e.g. chub) is disposed in a fixture, generally indicated at 20, which may be aluminum, steel or almost any plastic material having characteristics, in response to radiation from the accelerator 12, substantially corresponding to those of the article 16. The geometrical configuration of the fixture 20 in a planar direction corresponding to the direction of the radiation from the accelerator 12 complements the geometrical configuration of the article 16 such that the combined or composite configuration of the fixture 20 and the article 16 is essentially a square in section. The article 16 does not have to be disposed snugly within the fixture 20. The fixture 20 is movable with the article 14 past the accelerator 12.

In other words, the dimension of the composite article 16 and the fixture 20 in the direction of the radiation from the accelerator source 12 is substantially the same at every position in the direction of the radiation from the accelerator 12 when the composite is moved on the conveyor past the radiation in a direction substantially perpendicular to the direction of the radiation from the source. In this way, the radiation dosage of the article 16 at the position B is the same within the maximum and minimum limits as the radiation dosage of the article at the position A. This is also true for every position along the line between B and A and at every position along the extension of this line between A and E.

The fixture 20 has at the progressive positions characteristics, including a geometric shape, constituting the difference between substantially constant characteristics and the characteristics of the article at the progressive positions. The fixture 20 is disposed relative to the article 16 to provide the substantially constant characteristics for the combination of the article and the fixture at the progressive positions in the direction substantially perpendicular to the direction of the radiation from the accelerator 12. When there are irregularities in the geometric shape of the article, the fixture is disposed relative to the article to provide a substantially constant geometric shape defined by the combination of the article and the fixture at the progressive positions in the article.

Thus, applicant absorbs the radiant energy passing from the source 12 to the article 16 at the different positions in accordance with the irregularities of the article at the different positions so as to maintain the radiation dosage at the different positions in the article within the particular limits. Applicant provides for the radiation dosage from the source within the particular limits at the different positions in the article regardless of the irregularities in the characteristics of the article at the different positions. As will be seen, applicant compensates for, or complements, the irregularities in the characteristics of the article at the different positions in the article to provide substantial uniformity in the radiation dose at the different positions in the article within the particular limits.

Applicant also accomplishes the results specified in the previous paragraph (a) by providing a fixture having irregular characteristics, including an irregular geometric shape, at progressive positions to compensate for the differences in the irregularities of the characteristics, including the irregularities in the geometric shape, of the article at the progressive positions and (b) by disposing the fixture relative to the article to provide the combination of the article and the fixture with the compensating characteristics at the progressive positions in response to the radiation.

The fixture 20 has characteristics of receiving at the progressive positions different radiation doses per unit of distance of travel of the radiation through the fixture. The different radiation doses per unit of distance for the fixture 20 correspond to the different radiation doses per unit of distance for the article to maintain, within the particular limits at the progressive positions, the radiation dosage received by the article per unit of travel of the radiation through the article.

Figure 3:
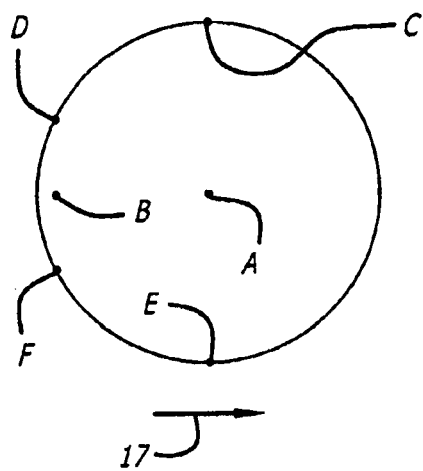
FIG. 3 is a simplified view indicating how a system of this invention provides for an irradiation of an article such as a chub regardless of irregularities in the characteristics, such as irregularities in the geometrical configuration, of the article, thereby to provide for an irradiation of the article at the different positions in the article with a dosage within particular minimum and maximum limits.
Figure 3:
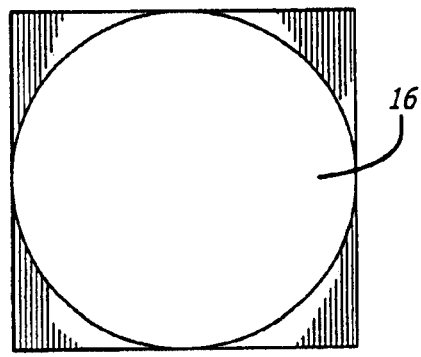
Figure 4:
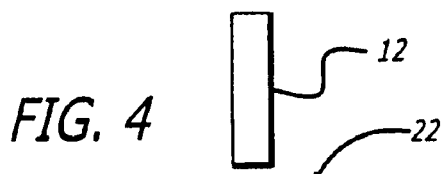
FIG. 4 is a simplified view showing how the system of this invention may include a fixture movable with the article past the radiation from the source to provide for an irradiation of the article at different positions of the article with a dosage within the particular minimum and maximum limits.

FIG. 4 illustrates a fixture, generally indicated at 22, which constitutes a modification of the fixture 20 shown in FIG. 3. The fixture 22 may constitute fixtures 22a on one side of the article 14 in the direction of the radiation from the accelerator 12 and fixtures 22b on the other side of the article in the direction of the radiation from the accelerator.

When the irregularities on the opposite sides of the article 14 are symmetrical, the irregularities in the fixtures 22a and 22b are also preferably symmetrical. However, if the irregularities in the geometrical shape on the opposite sides of the article 16 are not symmetrical, the irregularities in the geometric shape of the fixtures 22a on the opposite sides of the article are correspondingly not symmetrical and the irregularities in the geometric shape of the fixtures 22b on the opposite sides of the article are correspondingly not similar. As will be seen in FIG. 4, the irregularities in the geometrical shape of the fixtures 22a and 22b extend into the irregularities of the geometrical shape of the article 14. The fixtures 22a and 22b are movable with the article 14 past the radiation from the accelerator 12, preferably in a direction substantially perpendicular to the direction of the radiation from the accelerator 12. This is indicated by an arrow 23.

Figure 5:
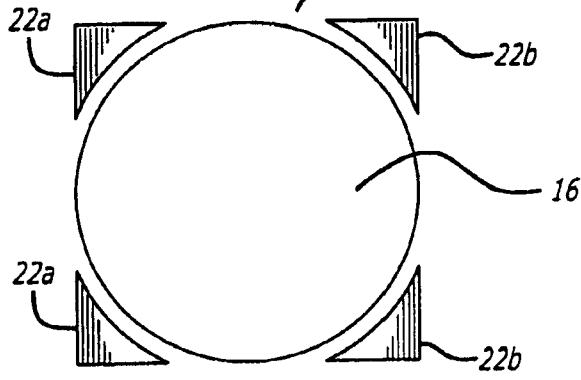
FIG. 5 is a simplified view indicating a modification of the fixture shown in FIG. 4.
Figure 5:
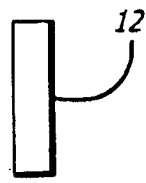
Figure 5:
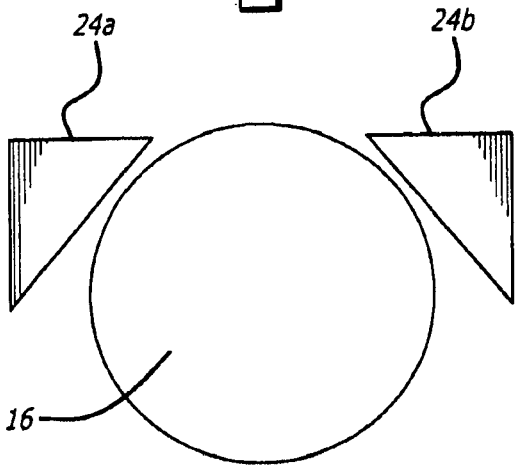

In FIG. 5, the fixtures 22a and 22b in FIG. 4 are combined to produce single fixtures 24a and 24b in FIG. 5. The fixture 24a has irregularities in its geometrical shape corresponding to a combination of the irregularities in the fixtures 22a in FIG. 4 at progressive positions substantially perpendicular to the direction of the radiation from the accelerator. In like manner, the fixture 24b has irregularities in its geometrical shape corresponding to a combination of the irregularities in the fixtures 22b in FIG. 4 at progressive positions substantially perpendicular to the direction of the radiation from the accelerator 12. The fixtures 24a and 24b are movable with the article 16 past the accelerator 12. The fixtures 24a and 24b absorb the radiation from the accelerator 12 in a manner similar to the combination of the absorptions provided by the fixtures 22a and 22b in FIG. 4. The fixtures 24a and 24b extend into the irregular shape of the article 16.

Although this invention has been disclosed and illustrated with reference to particular embodiments, the principles involved are susceptible for use in numerous other embodiments which will be apparent to persons of ordinary skill in the art. The invention is, therefore, to be limited only as indicated by the scope of the appended claims.

What is claimed is:

1. A method of irradiating an article from a radiation source where the article absorbs the radiation at different positions in the article in accordance with irregularities in the characteristics of the article at the different positions, including the steps of:

providing the radiation from the source in a particular direction, absorbing the radiation energy passing from the source to the article at the different positions in accordance with the irregularities in the characteristics of the article at the different positions to maintain the radiation dosage at the different positions in the article within particular minimum and maximum limits, and moving the article past the radiation from the source in a direction transverse to the particular direction, wherein the absorption is provided by a fixture having characteristics for absorbing the radiation energy at the different positions depending upon the irregularities in the characteristics of the article at the different positions.

2. A method as set forth in claim 1 wherein the article is moved past the radiation from the source in a direction substantially perpendicular to the particular direction and wherein the article has an irregular configuration and the fixture has a configuration which, when combined with the configuration of the article, provides a regular configuration.

3. A method of irradiating an article from a radiation source where the article absorbs the radiation from the source at different positions in the article in accordance with irregularities in the characteristics of the article at the different positions, including the steps of providing radiation from the source in a particular direction, moving the article past the radiation from the source in a second direction transverse to the particular direction, and providing for the absorption of the radiation energy from the source within particular minimum and maximum limits at the different positions in the article regardless of the irregularities in the characteristics of the article at the different positions, wherein the absorption of the radiation energy from the source within the particular minimum and maximum limits is controlled by a fixture having irregularities complementary at the different positions to the irregularities provided by the article at the different positions.

4. A method as set forth in claim 3 wherein the article is conveyed past the radiation source in a direction substantially perpendicular to the particular direction and at a substantially constant speed.

5. A method of irradiating an article from a irradiation source where the article absorbs the irradiation from the source at different positions in the article in accordance with irregularities in the characteristics of the article at the different positions, including the steps of providing radiation from the source in a particular direction, moving the article past the radiation from the source in a second direction substantially perpendicular to the particular direction and at a particular distance from the source; and while moving the article past the radiation at the particular distance from the source, compensating for the irregularities in the characteristics of the article at the different positions in the article to provide a uniformity in the radiation dosage at the different positions in the article within particular minimum and maximum limits, wherein the irregularities in the article at the different positions result from irregularities in the dimension of the article in the particular direction at the different positions and wherein the compensation is provided for the irregularities in the dimension of the article in the particular direction at the different positions.

6. A method as set forth in claim 5 wherein the article is conveyed past the radiation from the source in a direction substantially perpendicular to the particular dimension.

7. A method of irradiating an article from a radiation source where the article has irregular characteristics including an irregular shape and absorbs radiation passing through the article by an amount depending upon the characteristics, including the irregular geometrical shape, of the article and where the article has different radiation absorption characteristics at progressive positions in the article, including the steps of providing the radiation from the radiation source in a first direction, providing a fixture having irregular characteristics, including an irregular geometric shape, at progressive positions to compensate for the differences in the irregularities of the characteristics, including irregularities in the geometric shape, of the article at the progressive positions, disposing the fixture relative to the article to provide the combination of the article and the fixture with the compensating characteristics at the progressive positions in response to the radiation, and moving the combination of the article and the fixture at the progressive positions past the radiation source to irradiate the article at the progressive positions.

8. A method as set forth in claim 7 wherein the fixture has irregular characteristics at progressive positions dependent upon the irregularities in the characteristics of the articles at the progressive positions.

9. A method as set forth in claim 7 wherein the combination of the article and the fixture is moved past the radiation from the radiation source at a substantially constant speed in a direction substantially perpendicular to the direction of the radiation.

10. A method as set forth in claim 7 wherein the fixture is made from a material selected from a group consisting of a plastic and a metal and having characteristics of responding to the radiation substantially corresponding to the characteristics of the article in responding to the radiation.

11. A method as set forth in claim 10 wherein the combination of the article and the fixture is moved past the radiation from the radiation source at a substantially constant speed in a direction substantially perpendicular to the direction of the radiation from the source.

12. A method as set forth in claim 11 wherein a plurality of articles and a plurality of fixtures are moved past the radiation from the source and wherein, each of the articles and each of the associated fixtures is spaced from the adjacent articles and the adjacent fixtures by a particular distance within particular limits when the articles and the associated fixtures are moved past the radiation from the source.

13. A method of irradiating an article from a radiation source where the article has characteristics of absorbing at progressive positions different amounts of radiation per unit of distance of travel of radiation through the article, including the steps of:

providing radiation in a particular direction from the source, providing a fixture having characteristics of absorbing at the progressive positions in the fixture different amounts of radiation per unit of distance of travel of the radiation through the fixture, the different amounts of the absorbed radiation per unit of distance of the travel for the fixture corresponding to the different amounts of the absorbed radiation per unit of distance of travel for the article to maintain within particular minimum and maximum limits at the progressive positions the radiation dosage received by the article per unit of travel of the radiation through the article, disposing the fixture relative to the article to maintain within particular limits at the progressive positions the radiation dosage absorbed by the article per unit of distance of travel of the radiation through the article, and moving the combination of the article and the fixture at the progressive positions past the radiation from the radiation source to absorb the radiation from the source at the progressive positions.

14. A method of irradiating an article from a radiation source where the article absorbs radiation passing through the article by an amount depending upon the characteristics, including the geometric shape, of the article and where the article has different radiation absorption characteristics at progressive positions in the article, including the steps of:

providing the radiation from the radiation source in a first direction, providing a fixture having at the progressive positions characteristics, including a geometric shape, constituting a difference between substantially constant characteristics and the characteristics of the article at the progressive positions, disposing the fixture relative to the article to provide the substantially constant characteristics for the combination of the article and the fixture at the progressive positions, and moving the combination of the article and the fixture past the radiation from the source at the progressive positions.

15. A method as set forth in claim 14 wherein the article has irregularities in the dimension of the article in the first direction at the progressive positions and wherein the fixture has irregularities in the dimension of the fixture in the first direction at the progressive positions to provide a substantially constant dimension in the first direction at the progressive positions when the dimensions of the article and the fixture in the first direction at the progressive positions are combined.

16. A method as set forth in claim 14 wherein
the progressive positions in the article and the fixture are in a direction substantially perpendicular to the first direction.

17. A method of irradiating an article from a radiation source where the article absorbs radiation passing through the article by a dosage depending upon the characteristics, including the geometric shape, of the article and where the article has different radiation absorption characteristics at progressive positions in the article, including the steps of:
   providing the radiation from the radiation source in a first direction,
   providing a fixture with characteristics of absorbing the radiation corresponding to the absorption characteristics of the article in accordance with a difference between a substantially constant absorption and the absorption of the radiation by the article at the progressive positions,
   disposing the fixture and the article relative to each other to provide a substantially constant absorption at the progressive positions of the combination of the article and the fixture, and
   moving the combination of the article and the fixture past the radiation from the source in a direction substantially perpendicular to the first direction.

18. A method as set forth in claim 17 wherein
the characteristics in the article include the geometrical shape of the article and wherein the characteristics in the fixture include the geometrical shape of the fixture and wherein
the geometrical shape of the fixture provides the difference between the substantially constant characteristics and the irregularities in the geometrical shape of the article.

19. A method as set forth in claim 17 wherein
the fixture includes two (2) fixture portions respectively disposed on opposite sides of the article in the direction of the radiation from the source.

20. A method as set forth in claim 17 wherein
the fixture includes a single fixture having a geometrical shape providing the difference between a substantially constant geometric shape and the combination of the characteristics of the geometric shape of the article on the opposite sides of the article in the direction of the radiation from the source.

21. A method of irradiating in article from a radiation source where the article absorbs radiation by a dosage depending upon the characteristics of the article and where the article has different response characteristics to the radiation at progressive positions in the article, the absorption of the radiation in the article being dependent upon the composition and geometric shape of the article, including the steps of:
   providing the radiation from the source in a particular direction,
   providing a fixture having a composition with characteristics of absorbing the radiation corresponding to the absorption of the radiation by the composition of the article and having at progressive positions a geometric shape compensating for the geometric shape of the article,
   disposing the fixture relative to the article to provide a substantially constant geometric shape for the combination of the article and the fixture at progressive positions on the article and the fixture, and
   moving the combination of the article and the fixture past the radiation from the source in a direction substantially perpendicular to the radiation from the article.

22. A method as set forth in claim 21 wherein
the article is provided with irregularities in its geometric shape and wherein
the fixture is provided with irregularities in its geometric shape and wherein
the irregularities in the geometric shape of the fixture are complementary with the irregularities in the geometric shape of the article.

23. A method as set forth in claim 22 wherein
the irregularities in the geometric shape of the fixture are disposed on the opposite sides of the article in the direction of the radiation from the source.

24. A method as set forth in claim 22 wherein
the irregularities in the geometric shape of the fixture are disposed on a single side of the article in the direction of the radiation from the source.

25. In combination,
a radiation source for providing radiation in a particular direction,
an article having irregularities in its characteristics at different positions in the article where the irregularities in the characteristics produce non-uniformities in the absorption provided by the article to the radiation from the source,
a fixture having characteristics of absorbing the radiation energy from the source at the different positions, relative to the irregularities in the radiation absorption by the article at the different positions, to provide a substantial uniformity in the radiation dosage at the different positions in the article within particular minimum and maximum limits, and
a conveyor for moving the article and the fixture past the radiation from the source in a direction substantially perpendicular to the particular direction.

26. In a combination as set forth in claim 25 wherein
the irregularities in the characteristics of the article include irregularities in the geometrical shape of the article and wherein
the irregularities in the characteristics of the fixture include irregularities in the geometrical shape of the fixture.

27. In a combination as set forth in claim 25 wherein
the combination of the irregularities in the geometrical shapes of the article and the fixture provide substantially constant geometrical shapes within particular minimum and maximum limits.

28. In combination,
a radiation source for providing radiation in a particular direction,
an article having irregularities in its characteristics at different positions in the article where the irregularities in its characteristics affect the radiation dosage received by the articles at the different positions from the radiation source.
a fixture having irregularities in its characteristics to compensate for the irregularities in the characteristics of the article, and
a conveyor for moving the article and the fixture in a direction substantially perpendicular to the particular direction.

29. In a combination as set forth in claim 28 wherein
the irregularities in the characteristics of the article include at least irregularities in the geometrical shape of the article and wherein
the irregularities in the characteristics of the fixture include at least irregularities in the geometrical shape of the fixture.

30. In a combination as set forth in claim 28 wherein
the irregularities in the geometrical shape of the article include at least irregularities in the dimension of the article in the direction of the radiation from the source and wherein
the irregularities in the geometrical shape of the fixture include at least irregularities in the dimension of the fixture in the direction of the radiation from the source.

31. In a combination as set forth in claim 28 wherein
the article is moved past the radiation from the source at a substantially constant speed within particular limits.

32. In a combination as set forth in claim 28 wherein
the article is one of a sequence of articles and the fixture is one of a sequence of fixtures and the articles and the fixtures are moved in sequence past the radiation from the source at a substantially constant speed within particular limits and wherein
the articles and the fixtures are moved in sequence past the radiation from the source with a minimal separation between the articles within particular limits.

33. In combination for receiving radiation in a particular direction from a radiation source,
an article having irregularities in its characteristics at different positions in the article where the irregularities in the characteristics of the article cause irregularities to be produced in the radiation dose received by the article from the radiation source at the different positions, and
a fixture having characteristics of absorbing the radiation from the source at the different positions, in accordance with the energy characteristics of the article at the different positions, to provide substantially a uniformity in the radiation intensity at the different positions in the article within particular minimum and maximum limits.

34. In a combination as set forth in claim 33,
a source of radiation,
the fixture and the article being movable past the radiation from the source to receive radiation from the source.

35. In a combination as set forth in claim 34,
the article having irregularities in its characteristics at the different positions on opposite sides of the article and the fixture being provided with irregularities in its characteristics to compensate for the irregularities in the characteristics of the article and to provide substantially the uniformity in the radiation dosage at the different positions in the article within the particular minimum and maximum limits.

36. In a combination as set forth in claim 33,
the fixture including a first fixture portion on one side of the article and a second fixture portion on the opposite side of the article, the first and second fixture portions being separated from each other in a direction corresponding to the direction of the radiation from the source.

37. In a combination as set forth in claim 33,
the fixture being disposed on one side of the article and being provided with irregularities in its characteristics to compensate for the irregularities in the characteristics of the article on the opposite sides of the article and to provide substantially the uniformity in the radiation dosage at the different positions in the article within the particular minimum and maximum limits.

38. In a combination as set forth in claim 33,
the fixture including a first fixture portion on one of the opposite sides of the article and including a second fixture portion on the other of the opposite sides of the article, the first fixture portion having irregularities in its characteristics to compensate for the irregularities in the characteristics of the article on the one of the opposite sides of the article and the second fixture portion having irregularities in the characteristics of the article on the other of the opposite sides of the article.

39. In combination for receiving radiation in a particular direction from a radiation source,
an article having irregularities in its characteristics at different positions in the article, and
a fixture disposed relative to the article and having irregularities in its characteristics for compensating for the irregularities in the characteristics in the article at the different positions provide substantially a uniformity in the characteristics of the article within particular minimum and maximum limits.

40. In a combination as set forth in claim 39,
the article and the fixture being disposed relative to the radiation source to provide for the passage of the radiation from the source through the article and the fixture.

41. In a combination as set forth in claim 39,
the irregularities in the characteristics of the article including at least irregularities in the geometrical shape of the article and the irregularities in the characteristics of the fixture including at least irregularities in the geometrical shape of the fixture.

* * * * *